(12) United States Patent
Hsieh et al.

(10) Patent No.: US 11,131,644 B2
(45) Date of Patent: Sep. 28, 2021

(54) BIOSENSOR AND BIOLOGICAL DETECTION METHOD

(71) Applicant: Industrial Technology Research Institute, Hsinchu (TW)

(72) Inventors: Hui-Chu Hsieh, Changhua County (TW); Wen-Pin Hsieh, Miaoli County (TW); Nien-Jen Chou, Hsinchu (TW); Hui-Ju Shen, Hsinchu County (TW); Hui-Ling Peng, Hsinchu County (TW); Jing-Tsyr Lin, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 252 days.

(21) Appl. No.: 16/398,273

(22) Filed: Apr. 30, 2019

(65) Prior Publication Data

US 2019/0331631 A1    Oct. 31, 2019

Related U.S. Application Data

(60) Provisional application No. 62/664,287, filed on Apr. 30, 2018.

(30) Foreign Application Priority Data

Nov. 9, 2018  (TW) .................. 107139934

(51) Int. Cl.
*G01N 27/327* (2006.01)
*C12Q 1/00* (2006.01)
*G01N 33/543* (2006.01)

(52) U.S. Cl.
CPC ......... *G01N 27/3272* (2013.01); *C12Q 1/001* (2013.01); *G01N 27/3276* (2013.01); *G01N 33/54386* (2013.01)

(58) Field of Classification Search
CPC ........... G01N 27/3276; G01N 33/4836; G01N 33/48707
See application file for complete search history.

(56) References Cited

U.S. PATENT DOCUMENTS

| | | | |
|---|---|---|---|
| 4,429,343 A | * | 1/1984 | Freud .................. G01N 27/225 361/286 |
| 4,756,828 A | | 7/1988 | Litman et al. |

(Continued)

FOREIGN PATENT DOCUMENTS

| | | |
|---|---|---|
| CN | 2876778 | 3/2007 |
| CN | 1940558 | 4/2007 |

(Continued)

OTHER PUBLICATIONS

Dastider et al., "Impedance biosensor based in interdigitated electrode array for detection of *E.coli* O157:H7 in food products," Proc. SPIE 8369, Sensing for Agriculture and Food Quality and Safety IV, 83690Q (May 4, 2012) (Year: 2012).*

(Continued)

*Primary Examiner* — Alexander S Noguerola
(74) *Attorney, Agent, or Firm* — JCIPRNET

(57) ABSTRACT

A biosensor and a biological detection method are provided. The biosensor includes a substrate, a plurality of first and second electrodes in a strip shape, a material layer and a capture antibody. The substrate has a sampling region and a measuring region connected to the sampling region. The first and second electrodes are disposed on the substrate in the measuring region, and the first and second electrodes are arranged alternately with each other, wherein the first electrodes are connected in parallel with each other, and the second electrodes are connected in parallel with each other. The material layer is disposed on the substrate in the measuring region and covers the first and second electrodes, wherein the material layer has a channel exposing a portion (Continued)

of each of the first electrodes and a portion of each of the second electrodes, the channel is connected to the sampling region, and an extending direction of the channel is interlaced with an extending direction of the first electrodes and the second electrodes. The capture antibody is disposed on the first and second electrodes exposed by the channel.

10 Claims, 11 Drawing Sheets

(56) References Cited

U.S. PATENT DOCUMENTS

| | | | |
|---|---|---|---|
| 4,757,004 | A | 7/1988 | Houts et al. |
| 4,883,688 | A | 11/1989 | Houts et al. |
| 5,296,290 | A * | 3/1994 | Brassington ...... A61F 13/15699 442/405 |
| 5,382,341 | A * | 1/1995 | Aroutiounian ........ C23C 14/086 204/192.21 |
| 5,885,527 | A | 3/1999 | Buechler |
| 5,958,791 | A | 9/1999 | Roberts et al. |
| 8,337,683 | B2 | 12/2012 | Choi et al. |
| 9,919,313 | B2 * | 3/2018 | Lowe ............... G01N 33/54386 |
| 2004/0206399 | A1 * | 10/2004 | Heller ................ H01J 49/0018 137/375 |
| 2005/0023137 | A1 * | 2/2005 | Bhullar .................... C12M 1/00 204/403.1 |
| 2005/0158704 | A1 | 7/2005 | Tyvoll et al. |
| 2007/0054317 | A1 * | 3/2007 | Diebold ............. G01N 33/5306 435/7.1 |
| 2012/0122731 | A1 * | 5/2012 | Soh ........................ B03C 1/286 506/12 |
| 2017/0146530 | A1 | 5/2017 | Muraca et al. |

FOREIGN PATENT DOCUMENTS

| | | |
|---|---|---|
| CN | 201477070 | 5/2010 |
| CN | 102128932 | 7/2011 |
| CN | 206052034 | 3/2017 |
| TW | 200907337 | 2/2009 |
| TW | I468681 | 1/2015 |

OTHER PUBLICATIONS

Li et al., "An ELISA-based Amperometric Biosensor within a Photo-Patternable Adhesive Microfluidic Channel," Proceedings of the 10th IEEE International Conference on Nano/Micro Engineered and Molecular Systems (IEEE-NEEMS 2015) XIAN, China, Apr. 7-11, 2015 (Year: 2015).*
EPO computer-generated Englsih language translation of CN 2060520034 U downloaded Mar. 27, 2021, patented Mar. 29, 2017 (Year: 2017).*
"Office Action of Taiwan Counterpart Application", dated Jun. 12, 2019, pp. 1-6.
Donghoon Han et al., "Electrochemical Signal Amplification for Immunosensor Based on 3D Interdigitated Array Electrodes", Anal. Chem., Jun. 2014, pp. 5991-5998.
Jonathan P Metters et al., "New directions in screen printed electroanalytical sensors: an overview of recent developments". Analyst, Mar. 2011, pp. 1067-1076.
Moon-Keun Lee et al., "A Universal Spring-Probe System for Reliable Probing of Electrochemical Lab-on-a-Chip Devices", Sensors, Jan. 2014, pp. 944-956.
Carolina V. Uliana et al., "Fully disposable microfluidic electrochemical device for detection of estrogen receptor alpha breast cancer biomarker", Biosensors and Bioelectronics, Jan. 2018, pp. 156-162.
Jiri Kudr et al., "Microfluidic electrochemical devices for pollution analysis—A review", Sensors and Actuators B: Chemical, Jul. 2017, pp. 578-590.
Pedro Novo et al., "Control of sequential fluid delivery in a fully autonomous capillary microfluidic device", Lab Chip, Nov. 2012, pp. 641-645.
"Office Action of China Counterpart Application", dated Jun. 2, 2021, pp. 1-13.

* cited by examiner

BIOSENSOR AND BIOLOGICAL DETECTION METHOD

CROSS-REFERENCE TO RELATED APPLICATION

This application claims the priority benefit of U.S. provisional application Ser. No. 62/664,287, filed on Apr. 30, 2018, and Taiwan application Ser. No. 107139934, filed on Nov. 9, 2018. The entirety of each of the above-mentioned patent applications is hereby incorporated by reference herein and made a part of this specification.

TECHNICAL FIELD

The present disclosure relates to a sensor and a detection method, in particular, to a biosensor and a biological detection method.

BACKGROUND

Immunodetection is the use of specific binding between an antibody and an antigen to detect samples. Through the above-mentioned binding mechanism, it can be combined with the color reaction of an enzyme to show whether a specific antibody or antigen exists, and a quantitative analysis of the color shade can be performed through an analytical instrument. For example, qualitative and quantitative analysis of the above-mentioned color reaction can be performed by an ELISA reader.

However, the process of performing immunodetection by the color reaction is complicated, and the detection result is easily affected by the user's operation manner, so it is necessary to be operated by a professional. Thus, it is difficult to meet the requirements of small size, rapid detection, low cost, low energy consumption, easy operation and so on, which is not conducive to popularization in various needed places.

SUMMARY

The present disclosure provides a biosensor, including a substrate, a plurality of first electrodes in a strip shape, a plurality of second electrodes in a strip shape, a material layer and a capture antibody. The substrate has a sampling region and a measuring region connected to the sampling region. The first electrodes and the second electrodes are disposed on the substrate in the measuring region, and the first electrodes and the second electrodes are arranged alternately with each other, wherein the first electrodes are connected in parallel with each other, and the second electrodes are connected in parallel with each other. The material layer is disposed on the substrate in the measuring region and covers the first electrodes and the second electrodes, wherein the material layer has a channel exposing a portion of each of the first electrodes and a portion of each of the second electrodes, the channel is connected to the sampling region, and the extending direction of the channel is interlaced with the extending direction of the first electrodes and the second electrodes. The capture antibody is disposed on the first electrodes exposed by the channel and the second electrodes exposed by the channel.

The present disclosure further provides a biological detection method, including the following steps: providing the biosensor described above; providing a sample having an antigen to the sampling region and filling the channel with the sample such that the antigen binds to the capture antibody; providing a voltage difference between the first electrode and the second electrode to cause an electrochemical reaction between the antigen and the capture antibody; and collecting a current generated by the electrochemical reaction to obtain a concentration of the antigen corresponding to the above current.

The present disclosure still provides a biological detection method, including the following steps: providing the biosensor described above; providing a sample having an antigen to the sampling region and filling the channel with the sample such that the antigen binds to the capture antibody; providing a detection antibody with an enzyme to the sampling region and filling the channel with the detection antibody such that the antigen binds to the detection antibody; providing a cleaning solution into the channel; providing an enzyme substrate into the channel to cause the enzyme substrate to react with the enzyme; providing a voltage difference between the first electrode and the second electrode to cause an electrochemical reaction of an enzyme product produced by the enzyme reaction; and collecting a current generated by the electrochemical reaction to obtain a concentration of the antigen corresponding to the above current.

Based on the above, in the biosensor provided by the above embodiments, the first electrodes and the second electrodes are arranged alternately with each other, wherein the first electrodes are connected in parallel with each other, the second electrodes are connected in parallel with each other, and the extending direction of the channel is interlaced with the extending direction of the first electrodes and the second electrodes, so that the reaction efficiency and the electron transfer efficiency can be increased, thereby achieving the detection effects of high speed and high sensitivity.

In order to make the aforementioned and other objectives and advantages of the present disclosure comprehensible, embodiments accompanied with figures are described in detail below.

DETAILED DESCRIPTION OF DISCLOSED EMBODIMENTS

Figure 1A:
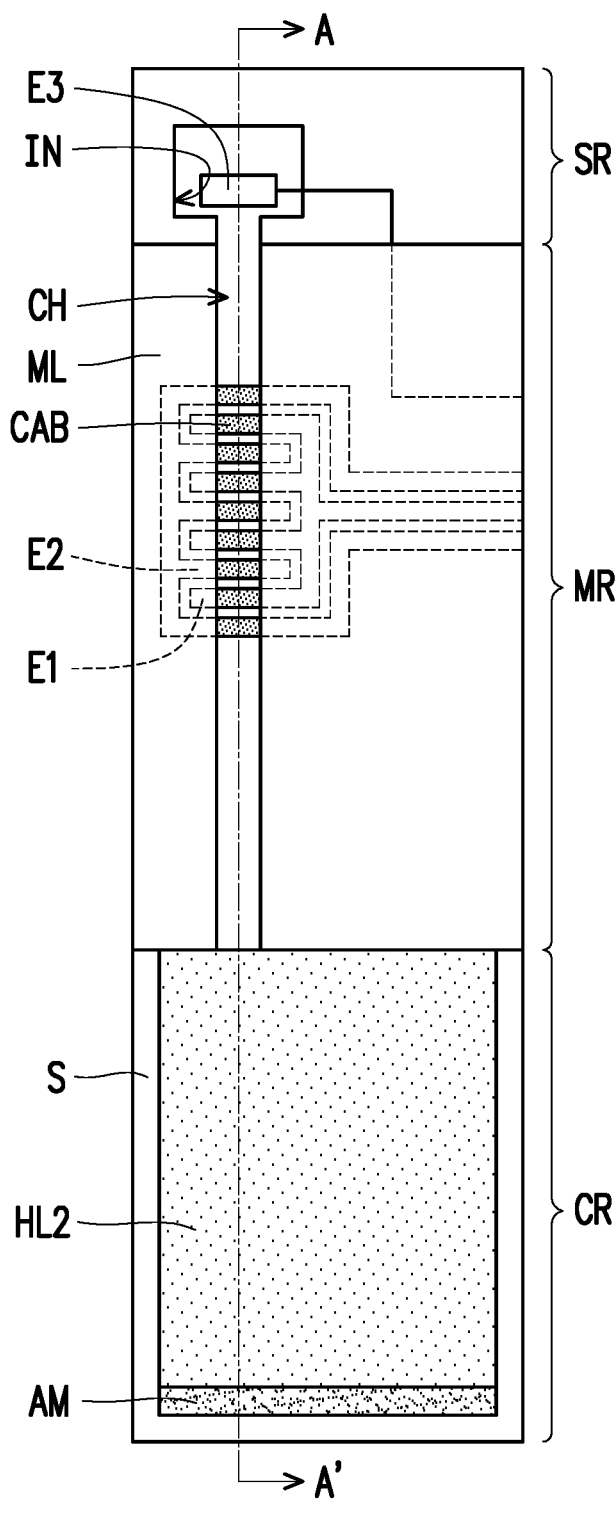
FIG. 1A is a schematic top view of a biosensor of one embodiment of the present disclosure.

The present disclosure is more fully described with reference to the drawings of the embodiments. However, the present disclosure may be embodied in a variety of different forms and should not be limited to the embodiments described herein. The thickness of layers and regions in the drawings will be exaggerated for clarity. The same or similar reference numerals indicate the same or similar elements, and the following paragraphs will not be repeated.

In one embodiment of the present disclosure, a biosensor having the advantages of no need for external power, easy rapid detection, high sensitivity, etc.

In one embodiment of the present disclosure, a biological detection method having the advantages of no need for external power, easy rapid detection, high sensitivity, etc.

Figure 1B:
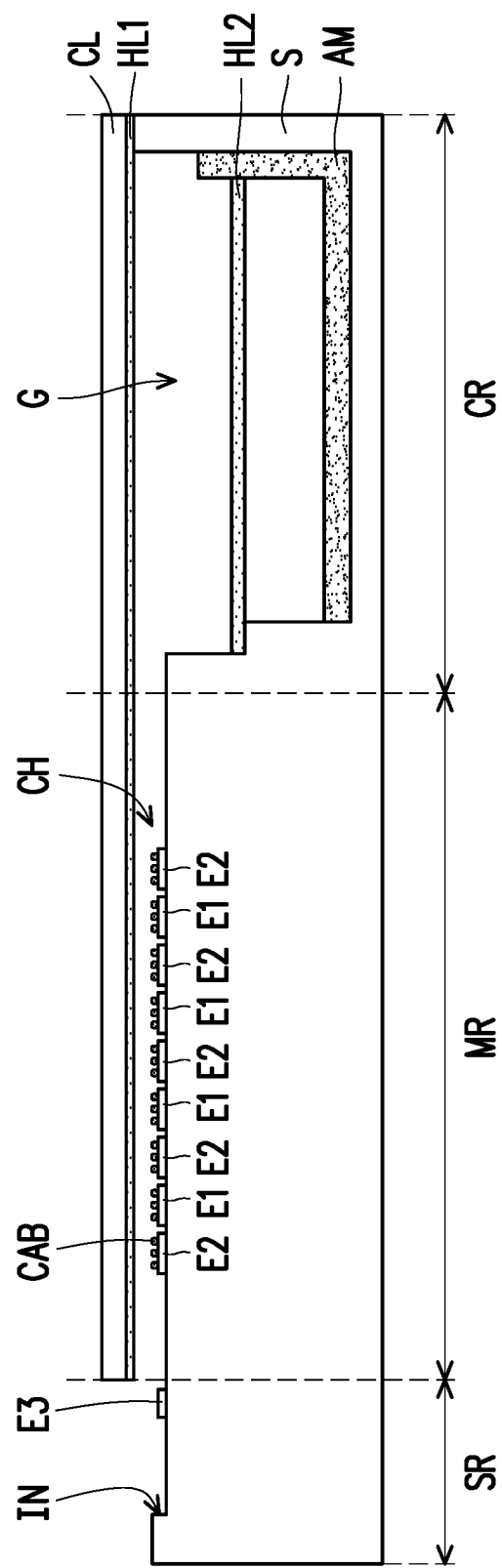
FIG. 1B is a schematic cross-sectional view taken along line A-A' in FIG. 1A.

FIG. 1A is a schematic top view of a biosensor of one embodiment of the present disclosure. FIG. 1B is a schematic cross-sectional view taken along line A-A' in FIG. 1A. It should be noted that in order to clearly illustrate the structure and relative relationship of a channel, first electrodes and the second electrodes, a cover and a hydrophilic layer are omitted in FIG. 1A.

Referring to FIG. 1A and FIG. 1B, the biosensor 100 may include a substrate S, a plurality of first electrodes E1 in a strip shape, a plurality of second electrodes E2 in a strip shape, a material layer ML and a capture antibody CAB.

The substrate S has a sampling region SR and a measuring region MR connected to the sampling region SR. The substrate S may be a flexible substrate, a rigid substrate, or a combination thereof. For example, the material of the substrate S may be polyethylene terephthalate (PET). In the present embodiment, the sampling region SR may include a groove IN disposed in the substrate S to accommodate a solution such as a sample, a reagent, a cleaning solution or an enzyme substrate, and allow the solution such as the sample, the reagent, the cleaning solution or the enzyme substrate to enter the biosensor 100 via the groove IN. In some embodiments, the groove IN may be disposed at the edge of the substrate S such that the above solution may enter the biosensor 100 in a lateral flow manner (which may be referred to as a lateral flow detection system), so that the capillarity can be used to drive the liquid forward, and thus, no additional power (such as a pump) is required.

In some embodiments, a third electrode E3 may be selectively disposed on the substrate S near the boundary of the measuring region MR in the sampling region SR to monitor the flow condition of the liquid entering the biosensor 100 by the groove IN. For example, when the solution such as the sample, the reagent, the cleaning solution or the enzyme substrate is not added or completely enters the measuring region MR, a signal measured by the third electrode E3 is maintained at the background signal. However, once the solution is added or remains in the sampling region SR, the signal measured from the third electrode E3 will be different from the background signal. That is, the flow condition of the liquid can be known by the signal change measured by the third electrode E3 to monitor whether the solution successfully flows from the sampling region SR to the measuring region MR. In the present embodiment, the third electrode E3 may be connected to an external metering device (e.g., an ammeter, a voltmeter or a potentiostat).

The plurality of first electrodes E1 and the plurality of second electrodes E2 may be disposed on the substrate S in the measuring region MR, and the first electrodes E1 and the second electrodes E2 may be arranged alternately with each other, so that the effect on electron transfer loss can be reduced while the contact area of the two electrodes is increased (the S/N ratio is increased), thereby improving the signal collection efficiency. In the present embodiment, the first electrodes E1 and the second electrodes E2 may be disposed on the substrate S in parallel and alternately arranged with each other, where the first electrodes E1 are connected in parallel with each other, and the second electrodes E2 are connected in parallel with each other, thereby increasing sensitivity by accumulating electronic signals in specific regions. For example, the first electrode E1 and the second electrode E2 may each be shaped as an interdigitated electrode. In FIG. 1A, the number of the first electrodes E1 and the second electrodes E2 is exemplified by 4 and 5 respectively, but the present invention is not limited thereto. In other embodiments, the number of first electrodes E1 and second electrodes E2 can be adjusted as needed. In the present embodiment, the first electrode E1 and the second electrode E2 may be connected to an external controlling device or metering device (e.g., a potentiostat).

In the present embodiment, one of the first electrode E1 and the second electrode E2 may be a working electrode; and the other of the first electrode E1 and the second electrode E2 may be a counter electrode. The materials of the first electrode E1 and the second electrode E2 may be a conductive material, for example, a metal, a metal oxide, or a combination thereof. In the present embodiment, the material of the first electrode E1 and the second electrode E2 may be gold (Au). In some embodiments, the first electrode E1 and the second electrode E2 may be formed by the following steps: firstly, forming an electrode material layer (not shown) on the surface of the substrate S; and then, patterning the electrode material layer to form the first electrode E1 and the second electrode E2. The method of forming the electrode material layer is, for example, plating. The method of patterning the electrode material layer is, for example, laser engraving. In other embodiments, the first electrode E1 and the second electrode E2 may be provided on the substrate S after the electrode material layer is first patterned to form the first electrode E1 and the second electrode E2.

The material layer ML may be disposed on the substrate S in the measuring region MR and cover a portion of the first electrode E1 and a portion of the second electrode E2, where the material layer ML includes a channel CH exposing a portion of each of the first electrodes E1 and a portion of each of the second electrodes E2. In the present embodiment, the channel CH is connected to the sampling region SR, so that the solution to be detected such as the sample, the cleaning solution or the enzyme substrate can flow from the sampling region SR provided with the groove IN into the measuring region MR through the capillarity of the channel CH. In the present embodiment, the material layer ML may be an adhesive material having a certain thickness attached to the substrate S to form the channel CH. In other words, the depth of the channel CH can be adjusted by controlling the thickness of the material layer ML. In other embodiments, the material layer ML may also be selectively disposed on the substrate S in the sampling region SR to form the groove IN.

In the present embodiment, the sum of the lengths of the overlapping portions of the channel CH with the first electrodes E1 and the second electrodes E2 in the extending direction of the channel CH may be greater than or equal to 0.8 cm, so that the biosensor 100 has a good S/N ratio, thereby increasing the detection limit of the biosensor 100. In some embodiments, the width of the channel CH may be 1.5 mm to 3 mm, so that the biosensor 100 has a good S/N ratio, thereby increasing the detection limit of the biosensor 100.

In the present embodiment, the extending direction of the channel CH needs to be interlaced with the extending direction of each of the first electrodes E1 and each of the second electrodes E2, so that the area of the electrode reaction region (i.e., the region where the first electrodes E1 exposed by the channel CH and the second electrodes E2 are exposed by the channel CH) can be increased and the electron transfer efficiency can be maintained. For example, if the extending direction of the channel CH is parallel to the extending direction of the first electrode E1 and the second electrode E2, for example, the first electrode E1 and the second electrode E2 are in elongated shape and parallel to the extending direction of the channel CH, such the design increases the transmission path of the electronic signal between the first electrode E1 and the second electrode E2, and the consumption of the electronic signal during the transmission is more significant, resulting in a decrease in electron transfer efficiency.

Figure 8A:
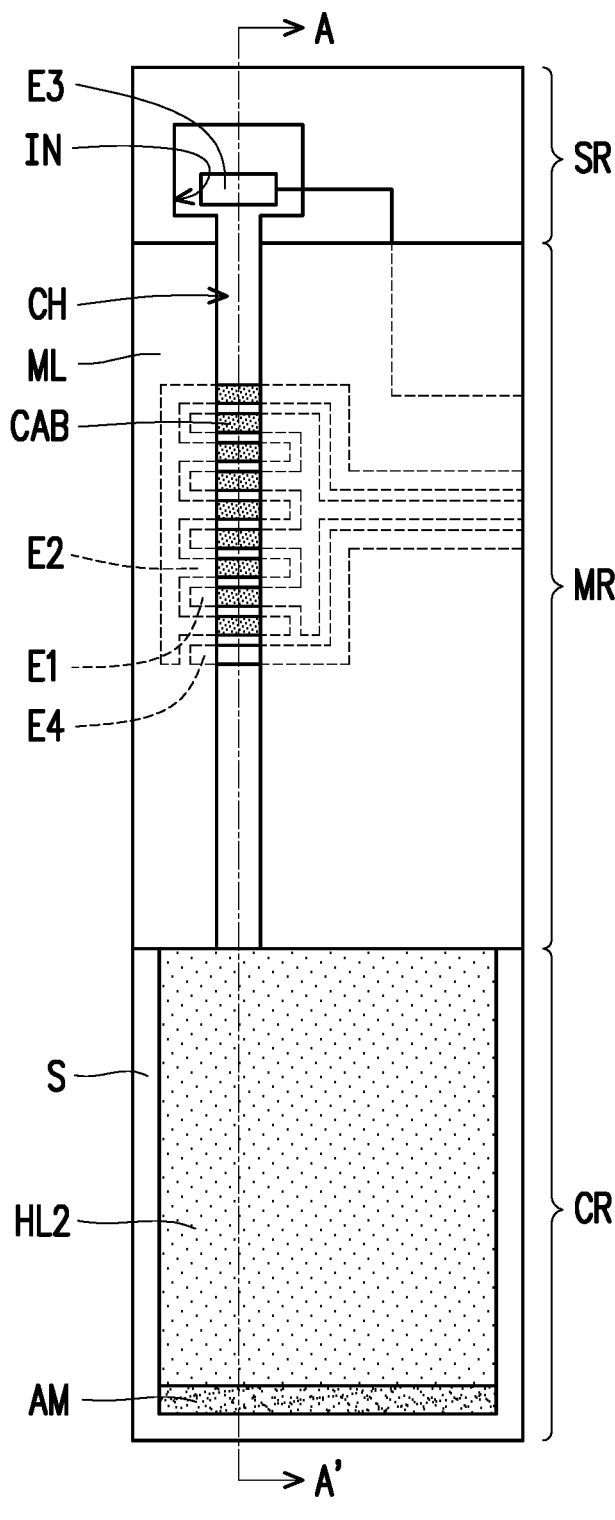
FIG. 8A is a schematic top view of a biosensor of another embodiment of the present disclosure.
Figure 8B:
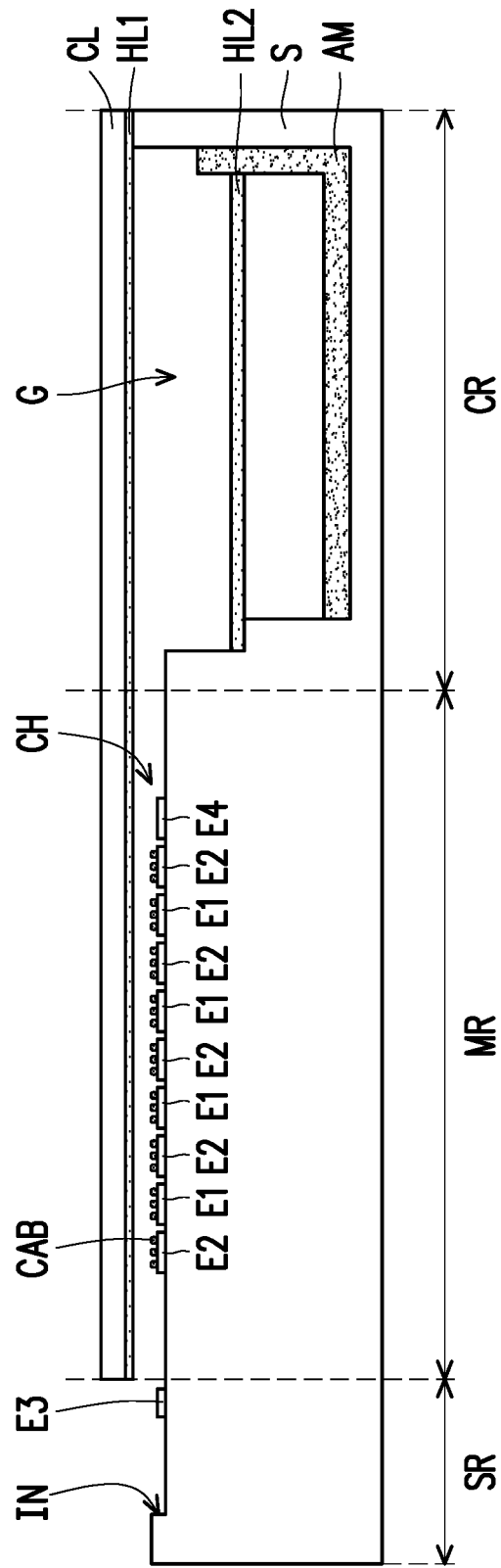
FIG. 8B is a schematic cross-sectional view taken along line A-A' in FIG. 8A.

In another embodiment, as shown in FIG. 8A and FIG. 8B, FIG. 8A is a schematic top view of a biosensor of another embodiment of the present disclosure, and FIG. 8B is a schematic cross-sectional view taken along line A-A' in FIG. 8A. The biosensor 100 may further include a fourth electrode E4, and the fourth electrode E4 may serve as a reference electrode to further improve the accuracy of the biosensor 100 in measurement. For example, the reference electrode can be silver/silver chloride (Ag/AgCl) or a saturated calomel electrode (SCE). In the present embodiment, the fourth electrode E4 may be disposed at a position adjacent to the second electrode E2 in the measuring region MR, but the present invention is not limited thereto. In other embodiments, the fourth electrode E4 may be placed at other suitable positions according to the design. In the present embodiment, the fourth electrode E4 may include a region exposed by the channel CH such that the sample to be detected can be in contact with the fourth electrode E4. In the present embodiment, the extending direction of the channel CH is interlaced with the extending direction of the fourth electrode E4, but the present invention is not limited thereto.

Referring to FIG. 1A and FIG. 1B, the capture antibody CAB is disposed on the first electrode E1 exposed by the channel CH and the second electrode E2 exposed by the channel CH. In some embodiments, the capture antibody CAB can be immobilized on the first electrode E1 and the second electrode E2 by the following steps: firstly, a thiol functional group is modified on the capture antibody CAB; and then, the modified capture antibody CAB is immobilized on the first electrode E1 and the second electrode E2. In the present embodiment, different antibodies may be used depending on different analytes to be detected. For example, in the case of dengue virus NS1 protein detection, the capture antibody CAB may be anti-NS1. It should be noted that the capture antibody CAB may be a biological antibody, a single-chain variable fragment antibody, a microantibody, an artificial antibody, or an antibody mimetic such as an aptamer, etc., and is not limited to those enumerated.

The biosensor 100 may further include a cover CL and a first hydrophilic layer HL1. The cover CL may be disposed on the material layer ML and cover the measuring region MR, and the first hydrophilic layer HL1 may be disposed on the surface of the cover CL facing the channel CH to cover the channel CH in the whole measuring region MR. In this way, the solution such as the sample, the cleaning solution or the enzyme substrate in the channel CH can be driven by the capillarity and the first hydrophilic layer HL1, and thus, the solution can flow from the sampling region SR to the measuring region MR via the channel CH without external power. In other words, the first hydrophilic layer HL1 may serve as one of the driving forces for driving the liquid flow in the channel CH, so that it is not necessary to additionally use a porous membrane such as a cellulose membrane (e.g., a nitrocellulose membrane) or paper to provide the driving force of the liquid flow, thereby avoiding the problem that the flow rate is inconsistent due to poor reproducibility of the porous membrane in the manufacturing process. In detail, if the cellulose membrane is used, the final enzyme substrate may be removed from the measuring region MR due to the inability to accurately control the absorption volume, resulting in the failure of the experiment. Therefore, in the present embodiment, the cellulose membrane may not be used, and the liquid can be stably stayed in the channel CH when it is finished, thereby avoiding affecting the experimental results. In other embodiments, the liquid flow rate in different regions can be designed by regionally setting the first hydrophilic layer HL1 according to actual needs.

In the present embodiment, the substrate S may further include a collecting region CR, where the collecting region CR is connected to the channel CH, and the measuring region MR may be arranged between the collecting region CR and the sampling region SR. In this way, the portion of the cleaning solution or sample used in the biological detection step that does not bind to the capture antibody CAB can be discharged into the collecting region CR to avoid interference of residues in the measuring region MR, thereby improving the sensitivity of the biosensor.

In some embodiments, the collecting region CR may include a groove (e.g., the groove G shown in FIG. 1A and FIG. 1B) disposed in the substrate S, so that the liquid discharged into the collecting region CR may be prevented from flowing back to the measuring region MR to cause interference. The volume of the groove G may be adjusted according to the volume of the solution such as the sample, the reagent or the cleaning solution required for the detection.

In the present embodiment, the biosensor 100 may further include an absorbing material AM disposed on the bottom and side walls of the groove G. The absorbing material AM is, for example, water absorbing cotton. The absorbing material AM can absorb the liquid discharged into the groove G to further prevent the liquid discharged into the collecting region CR from flowing back into the measuring region MR to cause interference. In addition, the absorbing material AM may also serve as one of the driving forces for driving the liquid flow in the channel CH. In the present embodiment, the biosensor 100 may further include a second hydrophilic layer HL2 disposed on the absorbing material AM to provide another driving force for driving the liquid flow in the channel CH.

In the case where the substrate S has the collecting region CR, the cover CL may cover the measuring region MR and the collecting region CR, and the first hydrophilic layer HL1 and the second hydrophilic layer HL2 are respectively disposed on the surface of the cover CL facing the channel CH and the absorbing material AM so as to further provide the driving force for driving the liquid in the channel CH. In this case, the liquid flow rate in the channel CH may be about 0.5 μL/s to 0.74 μL/s in the collecting region CR.

In some embodiments, in order for the capture antibody CAB to have sufficient time to capture the antigen in the sample, the channel CH can be designed as a meandering channel (e.g., an S-shaped channel) in the measuring region MR adjacent to the collecting region CR and combined with the non-hydrophilic cover CL such that the liquid in the channel CH in the region has a low flow rate (e.g., the liquid flow rate is about 0.17 μL/s), and thus, the capture antibody CAB can have sufficient time to capture the antigen in the sample.

Figure 2A:
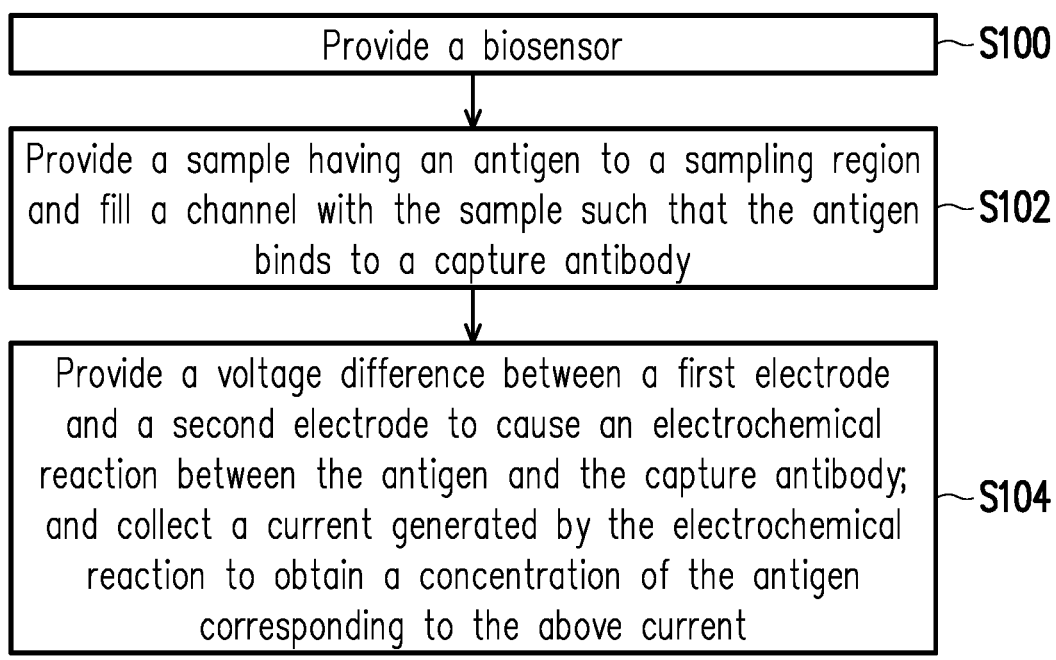
FIG. 2A is a flow chart of a biological detection method of one embodiment of the present disclosure.
Figure 2B:
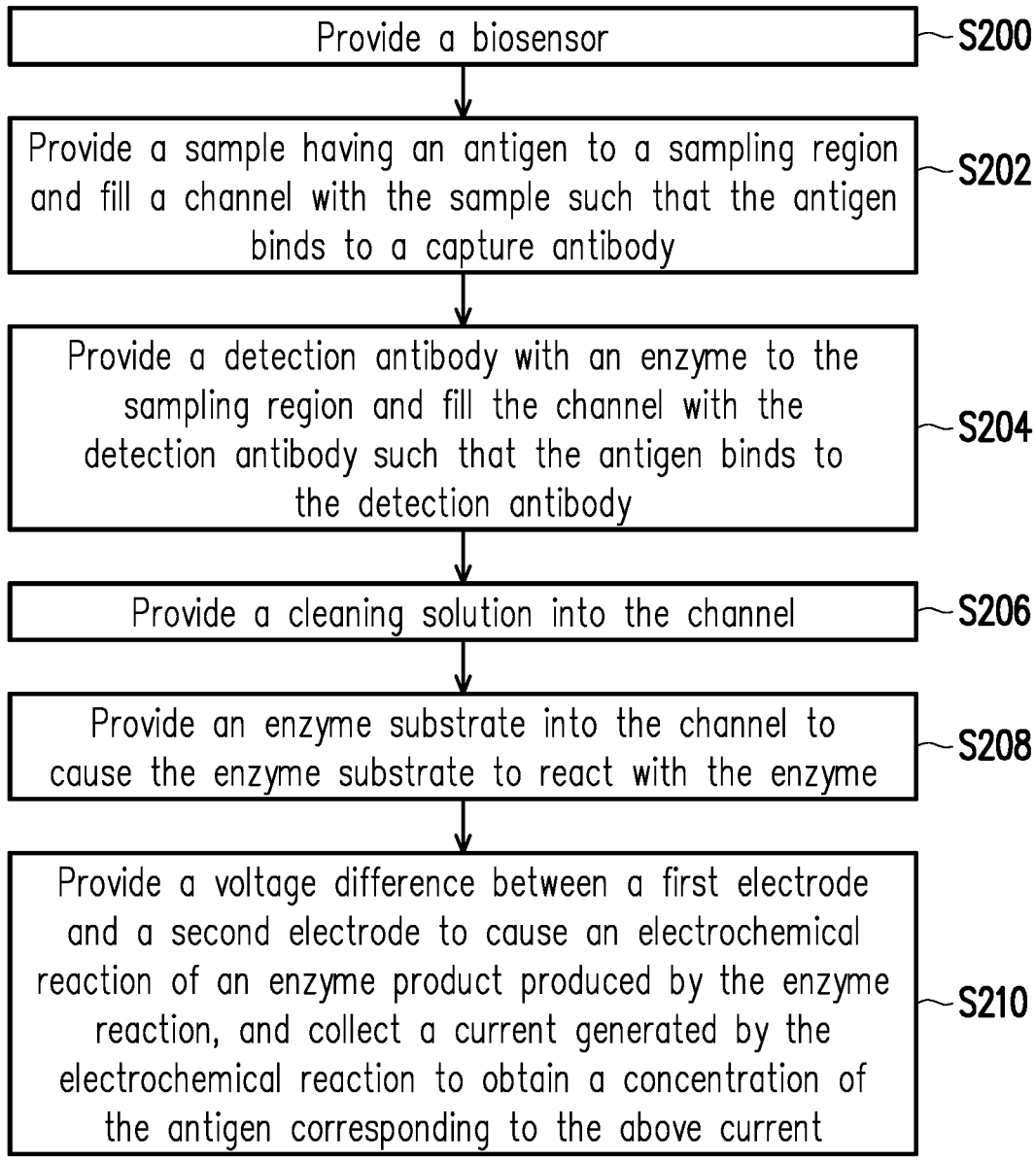
FIG. 2B is a flow chart of a biological detection method of another embodiment of the present disclosure.

FIG. 2A is a flow chart of a biological detection method of one embodiment of the present disclosure. FIG. 2B is a flow chart of a biological detection method of another embodiment of the present disclosure.

Hereinafter, a method of performing biological detection by the biosensor 100 described above will be described with reference to FIG. 2A and FIG. 2B, but the present disclosure is not limited thereto.

Referring to FIG. 2A, step S100 is performed to provide the biosensor 100.

Then, step S102 is performed to provide a sample having an antigen to the sampling region SR and fill the channel CH with the sample such that the antigen binds to the capture antibody CAB. For example, the sample placed on the sampling region SR may be in contact with the first electrode E1 exposed by the channel CH and the second electrode E2 exposed by the channel CH via the channel CH, thereby allowing the antigen in the sample to bind to the capture antibody CAB.

Then, step S104 is performed to provide a voltage difference between the first electrode E1 and the second electrode E2 to cause an electrochemical reaction between the antigen and the capture antibody CAB. For example, a voltage can be applied to one of the first electrode E1 and the second electrode E2 (e.g., the voltage is applied to the working electrode). Then, a current generated by the electrochemical reaction is collected to obtain a concentration of the antigen corresponding to the above current. In some embodiments, electrochemical signal detection can be performed by differential pulse voltammetry (DPV), but the present disclosure is not limited thereto. In some embodiments, the biological detection can be performed by an analyte of known concentration to obtain a calibration curve of concentration-to-current, so that after the current generated by the electrochemical reaction is collected, the corresponding analyte concentration can be known by the calibration curve.

Referring to FIG. 2B, the flow of the biological detection method is similar to the foregoing, but it should be noted that, in some embodiments, in addition to performing step S200 (providing the biosensor 100) and step S202 (providing a sample including an antigen to the sampling region SR and filling the channel CH with the sample such that that the antigen binds to the capture antibody CAB), after providing the sample including the antigen to the sampling region SR (step S202) and before providing the voltage difference between the first electrode E1 and the second electrode E2 (step S210), step S204 is performed to provide a detection antibody with an enzyme to the sampling region SR and fill the channel CH with the detection antibody such that the antigen binds to the detection antibody. In detail, the binding site of the antigen to the capture antibody CAB on the antigen and the binding site of the antigen to the detection antibody on the antigen are not the same, so the binding of the detection antibody and the capture antibody CAB to the antigen does not interfere with each other. At this time, a sandwich structure is formed among the antigen, the detection antibody and the capture antibody CAB. Thereafter, step S206 may be performed to introduce a cleaning solution into the channel CH to remove the interfering substance in the sample or the antigen not captured by the capture antibody CAB from the measuring region MR so as to reduce the interference factor of the biological detection, thereby increasing the sensitivity of the biosensor 100. In the present embodiment, the cleaning solution may be a buffer solution or deionized water. For example, the buffer solution may be PBST (i.e., a buffer solution containing phosphate buffered saline (PBS) and Tween 20).

After rinsing, the sandwich structure of the capture antibody CAB, the antigen and the detection antibody is immobilized on the electrode. Then, after introducing the cleaning solution into the channel CH (step S206) and before providing a voltage difference between the first electrode E1 and the second electrode E2 (step S210), step S208 may be performed to provide the enzyme substrate to the channel CH to cause the enzyme substrate to react with the enzyme on the detection antibody. In detail, the enzyme substrate reacts with the enzyme on the detection antibody to hydrolyze and produce an electroactive enzyme product. Finally, step S210 is performed to provide a voltage difference between the first electrode E1 and the second electrode E2 to cause an electrochemical reaction of an enzyme product produced by the enzyme reaction, and collect the current generated by the electrochemical reaction to obtain a concentration of the antigen corresponding to the above current. In detail, the enzyme product is activated to generate a current, and the concentration of the antigen is calculated by the magnitude of the current. In the present embodiment, the detection antibody with an enzyme may be a detection antibody with alkaline phosphatase (ALP). In the present embodiment, the enzyme substrate may be 4-aminophenyl phosphate (pAPP). It should be noted that the detection antibody with the enzyme may be a biological antibody, a single-chain variable fragment antibody, a micro-antibody, an artificial antibody, and an antibody mimetic such as an aptamer, etc., and is not limited to those enumerated.

Based on the biological detection method flow of the above two different embodiments, it can be known that the biosensor 100 can infer the antigen concentration by the current generated by the electrochemical reaction of the capture antibody CAB, and can also infer the antigen concentration by additionally binding the enzyme to the antigen through the current signal of the enzyme product generated by the enzyme reaction, but is not limited thereto.

Based on the above, in the biosensor 100 of the above embodiment, the first electrode E1 and the second electrode E2 are arranged alternately with each other, where the first electrodes E1 are connected in parallel with each other, the second electrodes E2 are connected in parallel with each other, and the extending direction of the channel CH is interlaced with the extending direction of the first electrodes E1 and the second electrodes E2, so that the reaction efficiency (e.g. immunoaffinity reaction efficiency) and the electron transfer efficiency can be increased, thereby achieving the detection effects of high speed and high sensitivity.

The characteristics of the present invention will be more specifically described below with reference to the biosensors of Experimental Example 1 and Comparative Examples 1 and 2. Although the following experimental examples are described, materials used, their amounts and ratios, processing details, processing procedures, and the like can be appropriately changed without exceeding the scope of the present invention. Therefore, the present invention should not be construed restrictively by the embodiments described below.

Experimental Example 1

The biosensor of Experimental Example 1 includes a plurality of working electrodes in a strip shape and a plurality of counter electrodes in a strip shape, where the plurality of working electrodes is connected in parallel with each other, the plurality of counter electrodes is connected in parallel with each other, the working electrodes and the counter electrodes are alternately arranged with each other, and the extending direction of the working electrodes and the counter electrodes is interlaced with the extending direction of the channel, where the capture antibody is disposed on the working electrode and the counter electrode exposed by the channel (as in the embodiment of FIG. 1A and FIG. 1B).

Comparative Example 1

The biosensor of Comparative Example 1 includes an elongated working electrode and an elongated counter electrode, and the extending direction of the working electrode and the counter electrode is parallel to the extending direction of the channel, where the capture antibody is disposed on the working electrode and the counter electrode exposed by the channel.

Comparative Example 2

A biosensor of a test strip for general immunodetection (only a single working electrode and a single counter electrode) is used. The test strip for general immunodetection is not provided with a channel or groove, the solution such as a sample, a cleaning solution or an enzyme substrate needs to first react in a reaction tank, and the measurement is performed directly after the capture antibody captures the antigen or after the reaction of the enzyme and the enzyme substrate is completed.

Experiment 1

Figure 3:
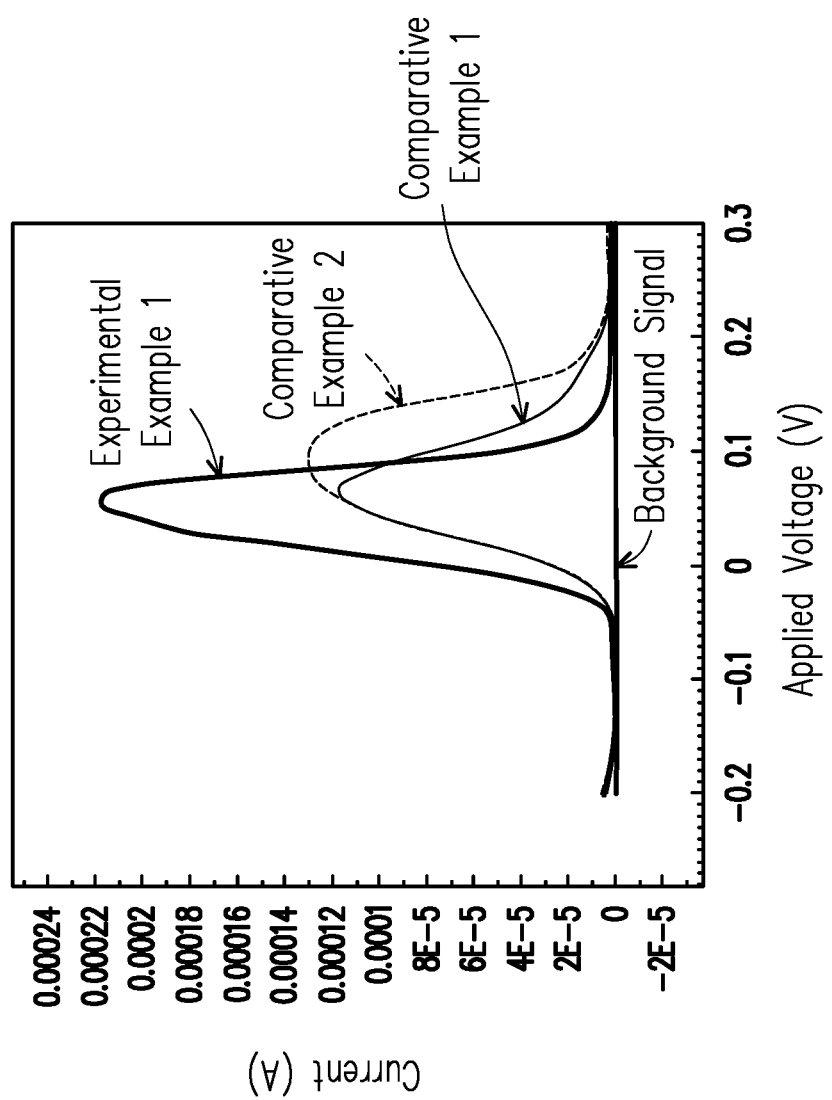
FIG. 3 is a curve diagram showing voltage versus current for electrochemical analysis using different biosensors.

Using the biosensors of Experimental Example 1 and Comparative Examples 1 and 2, the enzyme substrate (pAPP) was catalyzed in the case where the enzyme (ALP) concentration was 0.8 µg/ml, and the results are shown in FIG. 3. FIG. 3 is a curve diagram showing voltage versus current for electrochemical analysis using different biosensors. It should be noted that the background signal in FIG. 3 is the signal value of the sample containing only the enzyme substrate (pAPP).

As shown in FIG. 3, in the case of the same enzyme (ALP) and enzyme substrate (pAPP) concentrations, the sensitivity of Experimental Example 1 was superior to that of Comparative Example 1 and Comparative Example 2, and the sensitivity of Comparative Example 1 was similar to the sensitivity of Comparative Example 2.

Experiment 2

The biosensors of Experimental Example 1 and Comparative Example 2 were used to catalyze the enzyme substrate (pAPP) at different enzyme (ALP) concentrations at different ambient temperatures (25° C. and 37° C.), and the results are shown in Table 1. In Table 1, the signal-to-background ratio (1/0) represents the ratio of the enzyme (ALP) concentration of 1 ng/ml to the enzyme (ALP) concentration of 0 ng/ml; and the signal-to-background ratio (5/0) represents the ratio of the enzyme (ALP) concentration of 5 ng/ml to the enzyme (ALP) concentration of 0 ng/ml.

TABLE 1

| | Temperature (° C.) | Applied Voltage (V) | Current Signal Value (A) | | | Signal-to-Background Ratio (1/0) | Signal-to-Background Ratio (5/0) |
| | | | ALP concentration of 0 ng/ml | ALP concentration of 1 ng/ml | ALP concentration of 5 ng/ml | | |
|---|---|---|---|---|---|---|---|
| Experimental Example 1 | 37 | 0.0571 | 4.22E−07 | 5.90E−07 | 1.16E−06 | 1.40 | 2.75 |
| Experimental Example 1 | 25 | 0.0491 | 2.44E−06 | 3.01E−06 | 6.60E−06 | 1.23 | 2.71 |
| Comparative Example 2 | 25 | 0.0571 | 1.34E−06 | 1.44E−06 | 1.87E−06 | 1.08 | 1.4 |

As can be seen from Table 1, the signal-to-background ratio (also referred to as the S/N ratio) of Experimental Example 1 is superior to the signal-to-background ratio of Comparative Example 2.

Experiment 3

The biosensor of Experimental Example 1 was used for biological detection (taking dengue virus NS1 protein as an example), and the steps were as follows: Firstly, the capture antibody (anti-NS1) was immobilized to the electrode, and a sample, a cleaning solution and an enzyme substrate were respectively added to the sampling region, where the sample was an antigen analyte having a volume of about 40 µL and a detection antibody with an alkaline phosphatase enzyme. Then, after the sample was injected for about 1 minute, the cleaning solution and the enzyme substrate sequentially flowed through the working electrode and the counter electrode in the measuring region, and 15 minutes after the injection of the enzyme substrate, the differential pulse voltammetry (DPV) can be used for electrochemical detection. Experiment 3 was electrochemical detection of samples of different dilution ratios (10-fold, 40-fold and 160-fold), and the experimental results are shown in FIG. 4.

Figure 4:
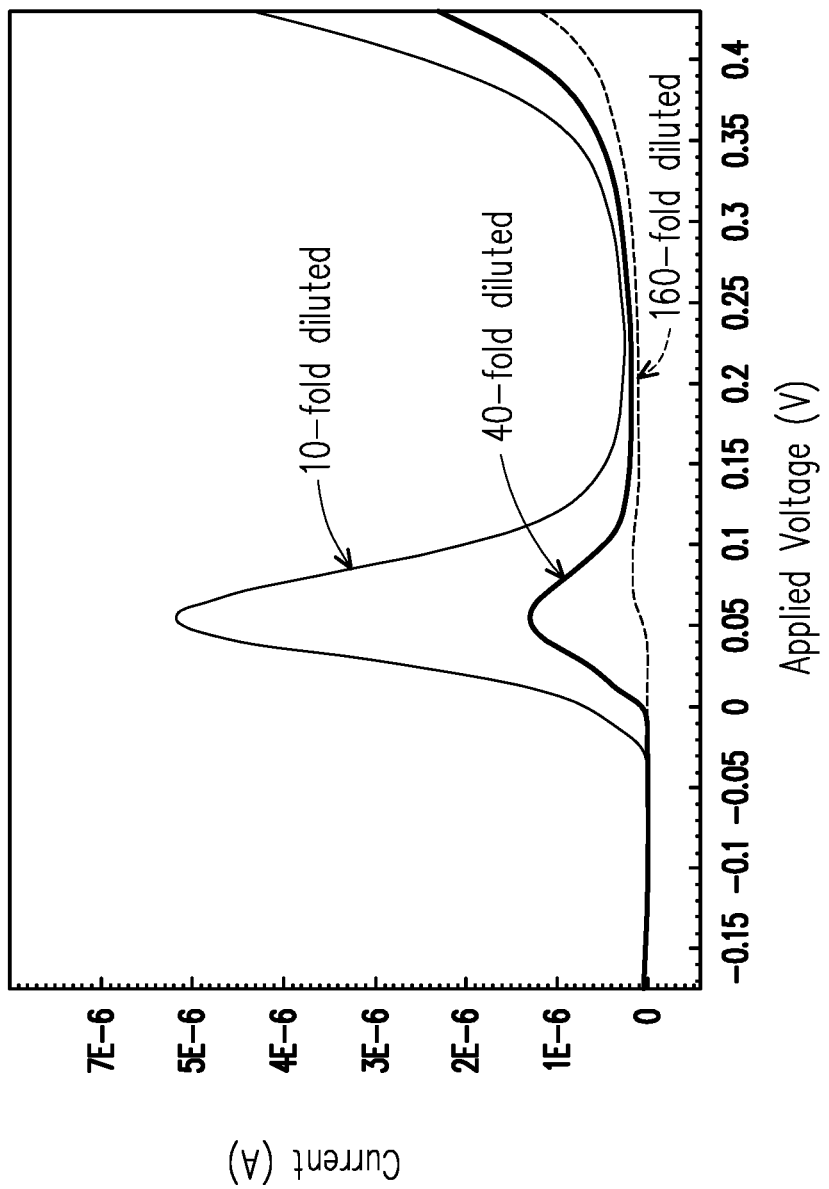
FIG. 4 is a diagram showing voltage versus current for electrochemical analysis of samples of different dilution ratios by using the biosensor of Experimental Example 1 and the biological detection method of one embodiment of the present disclosure.

FIG. 4 is a diagram showing voltage versus current for electrochemical analysis of samples of different dilution ratios by using the biosensor of Experimental Example 1 and the biological detection method of one embodiment of the present disclosure.

As shown in FIG. 4, the biosensor of Experimental Example 1 can successfully distinguish 10-fold, 40-fold, and 160-fold diluted antigen analytes within only 1 minute of antibody and antigen reaction time, demonstrating that the biosensor of Experimental Example 1 can be used for qualitative and quantitative analysis.

Experiment 4

The biosensor of Comparative Example 2 was used for biological detection (taking dengue virus NS1 protein as an example), and the steps were as follows: Firstly, the capture antibody (anti-NS1) was immobilized to the electrode and the sample were added to a reaction tank and subjected to shaking reaction for 20 minutes, where the sample includes an antigen analyte and a detection antibody with an alkaline phosphatase enzyme. Then, manual washing was performed, the enzyme substrate was added, and after the enzyme and the enzyme substrate reacted for 15 minutes, electrochemical detection was performed using a test strip for general immunodetection (only a single working electrode and a single counter electrode) by differential pulse voltammetry (DPV). Experiment 4 was electrochemical detection of samples of different dilution ratios (10-fold, 40-fold and 160-fold), and the experimental results are shown in FIG. 5.

Figure 5:
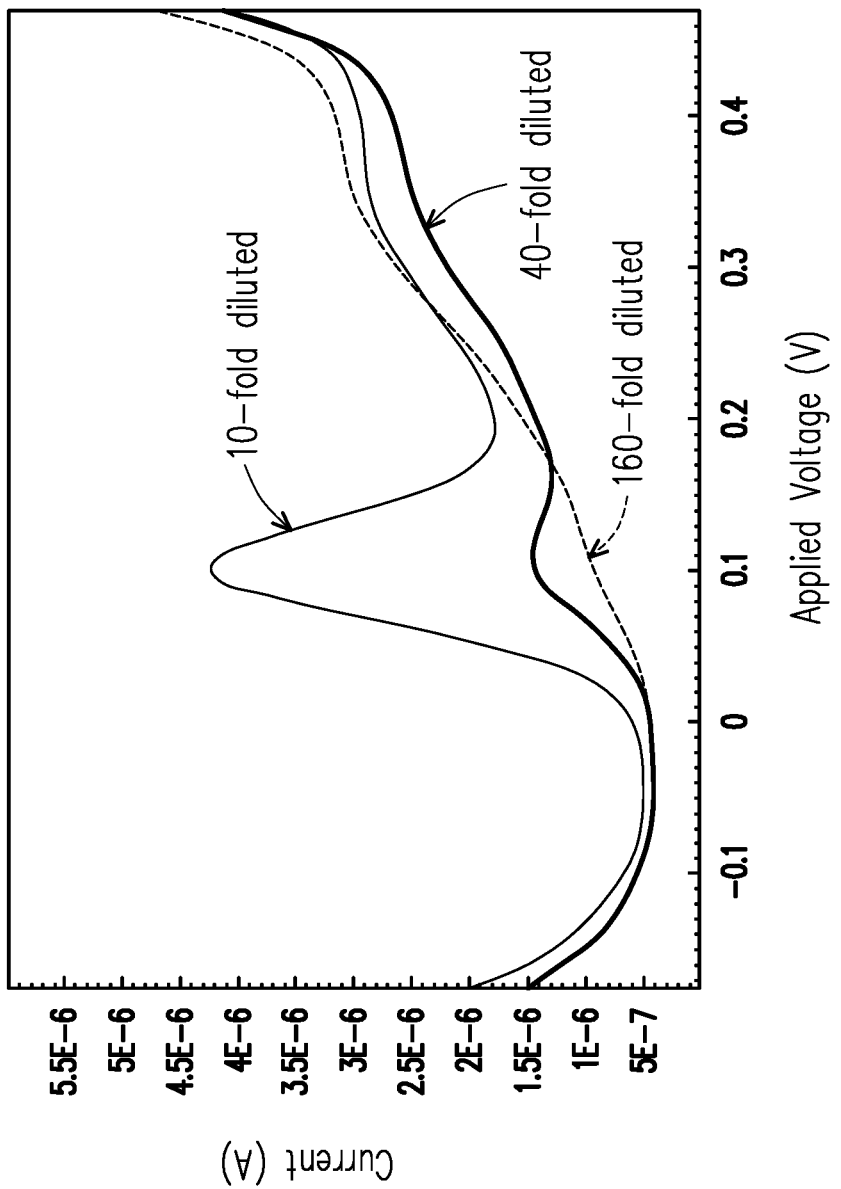
FIG. 5 is a diagram showing voltage versus current for electrochemical analysis of samples of different dilution ratios by using the biosensor of Comparative Example 1 by a shaking reaction.

FIG. 5 is a diagram showing voltage versus current for electrochemical analysis of samples of different dilution ratios by using the biosensor of Comparative Example 2 by a shaking reaction.

By comparing the experimental results shown in FIG. 4 and FIG. 5, the biosensor of Experimental Example 1 had a more significant signal change for the 10-fold, 40-fold and 160-fold diluted antigen analytes. Further, in the reaction time required for the experiment, the time required for Experimental Example 1 was also less than that of Comparative Example 2, and was about 1/20 of Comparative Example 2.

<Effect of Electrode Length on Biological Detection>

Experiment 5

Figure 6:
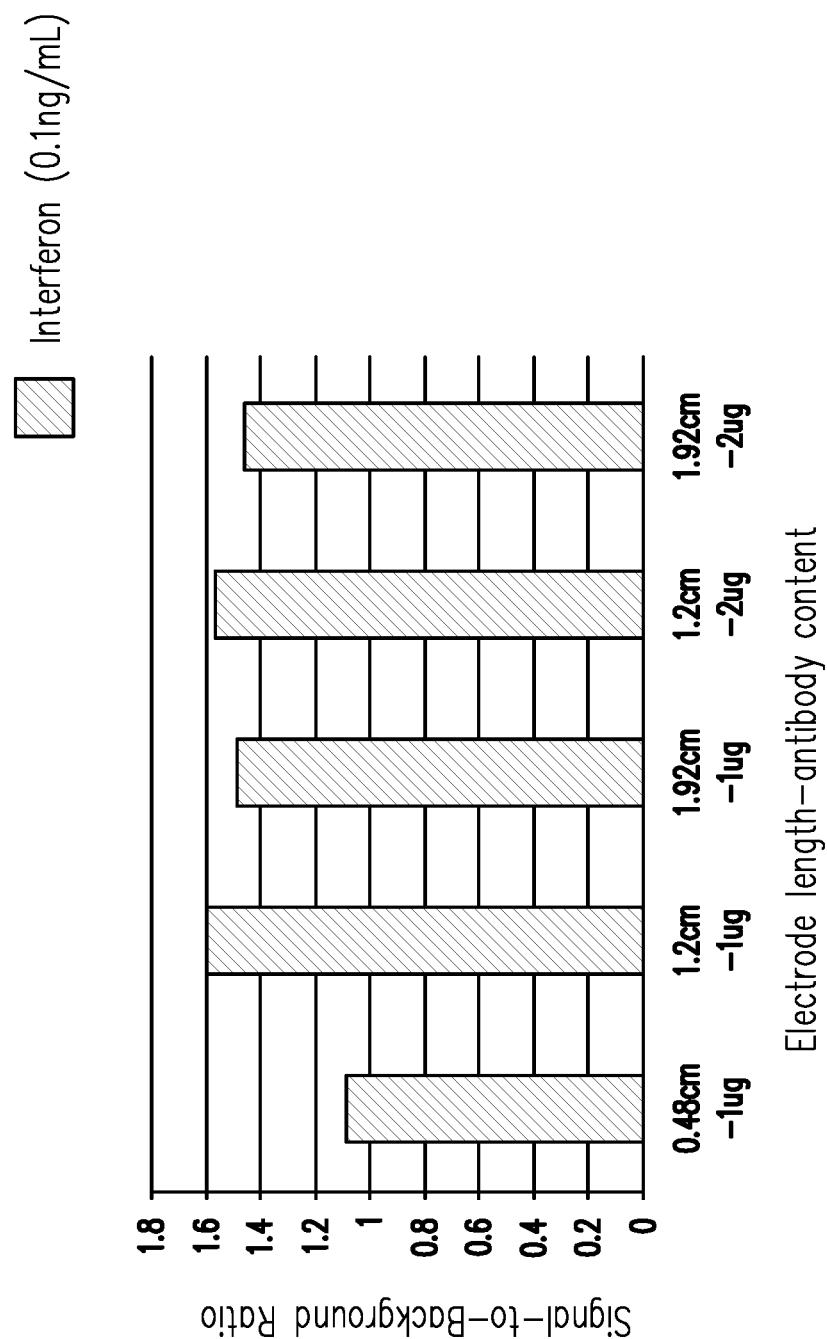
FIG. 6 is a diagram showing the effect of an electrode length in the measuring region on the sensitivity of biological detection.

The electrode length (0.48 cm, 1.2 cm, and 1.92 cm) used in the biosensor of Experimental Example 1 was changed to perform biological detection (taking interferon gamma as an example) to investigate the effect of the electrode length on biological detection. The electrode length referred to herein means the length of the overlapping portion of the channel and the electrode in the extending direction of the channel. The detection steps were as follows: Firstly, a capture antibody capable of capturing interferon was immobilized on the electrode, and 40 μL of a sample, 40 μL of a detection antibody (biotin conjugated detection antibody) having a concentration of 125 ng/ml, 40 μL of an enzyme (streptavidin conjugated alkaline phosphatase), 500 μL of a cleaning solution (PBST) and 50 μL of an enzyme substrate (p-aminophenyl phosphate, pAPP) were sequentially added to the sampling region. 40 μL of the sample or reagent flowed to the electrode in the measuring region via the channel within about 3 minutes. After 15 minutes of waiting after all the above reagents were completely added, electrochemical detection was performed by differential pulse voltammetry (DPV). The experimental results are shown in FIG. 6. FIG. 6 is a diagram showing the effect of electrode length in the measuring region on the sensitivity of biological detection.

The detection results of the electrode lengths of 1.2 cm and 1.92 cm with different capture antibody contents (1 μg and 2 μg) are also shown in FIG. 6. For example, the 0.48 cm-1 μg shown in FIG. 6 indicates that the electrode length is 0.48 cm; and the capture antibody content is 1 μg.

As shown in FIG. 6, the electrode lengths of 1.2 cm and 1.92 cm can successfully distinguish between 0 ng/mL and 0.1 ng/mL of interferon, while the 0.48 cm electrode cannot clearly distinguish, where the electrode length of 1.2 cm has a good signal-to-background ratio. The results of Experiment 5 show that when the electrode length is too small, it will affect the judgment of the signal. Once the electrode length reaches the appropriate value or more, if the electrode length is greater than or equal to 0.8 cm, since the electrical signals generated by the electrochemical reaction of the capture antibody are collected in a sufficient electrode length, accurate measurement results can be obtained.

<Effect of Sample Flow Time on Biological Detection>

Experiment 6

The biosensor of Experimental Example 1 was used for biological detection (taking IgM induced by Zika virus infection as an example), and the steps were as follows: Firstly, a capture antibody (anti-IgM) was immobilized on the electrode, and a serum sample, an antigen (taking Zika virus NS1 as an example), a detection antibody, a cleaning solution and an enzyme substrate were respectively into the sampling region, where the sample was about 40 μL of serum, 40 μL of antigen and 20 uL of detection antibody with an alkaline phosphatase enzyme. Then, after the sample, the reagent cleaning solution and the enzyme substrate sequentially flowed through the working electrode and the counter electrode in the measuring region and 15 minutes of waiting after the enzyme substrate was injected, electrochemical detection can be performed by differential pulse voltammetry (DPV). Experiment 6 was electrochemical detection of serum containing different anti-Zika virus IgM concentrations, where NC(−) is a negative sample detection result; and S6(+) is a positive sample detection result. The experimental results are shown in FIG. 7.

Figure 7:
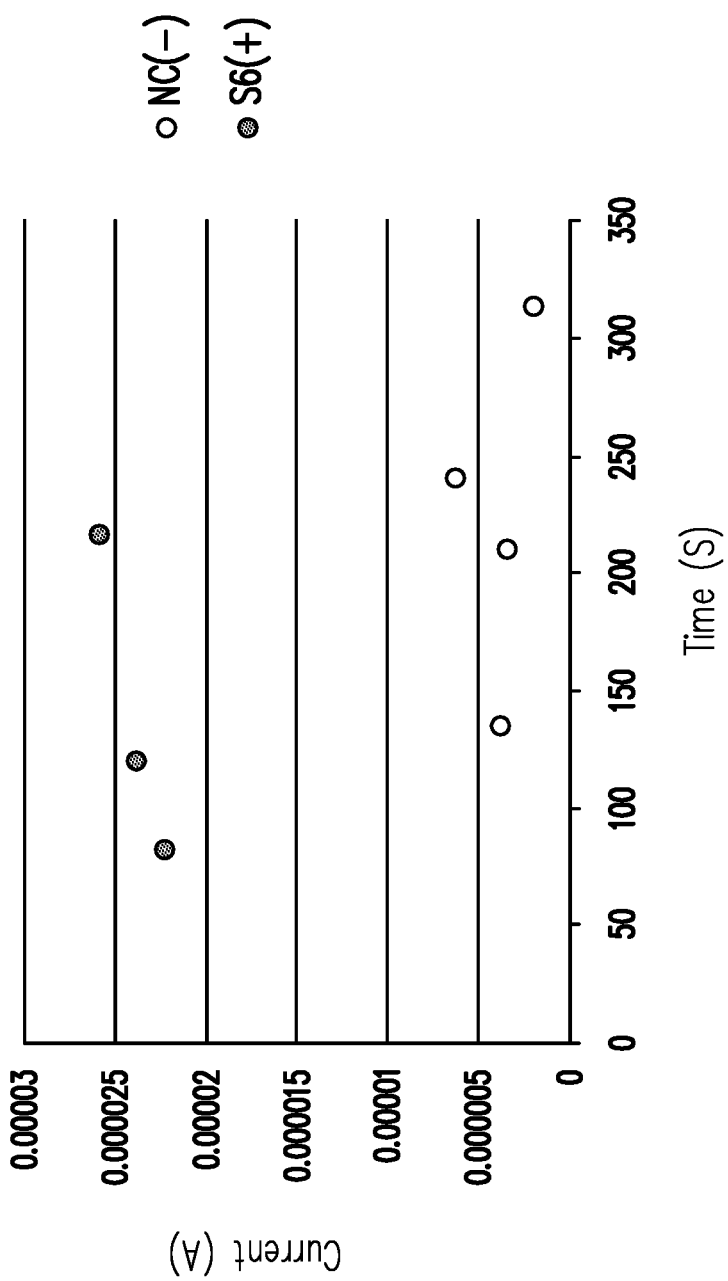
FIG. 7 is a diagram showing current versus time for electrochemical analysis for flow times of different sample by using the biosensor of Experimental Example 1 and the biological detection method of one embodiment of the present disclosure.

FIG. 7 is a diagram showing current versus time for electrochemical analysis for flow times of different sample by using the biosensor of Experimental Example 1 and the biological detection method of one embodiment of the present disclosure. As shown in FIG. 7, in the biosensor of Experimental Example 1, the determination of the measured current intensity and the high and low concentrations was not affected by the sample flow time, demonstrating that the biosensor of Experimental Example 1 can perform portable rapid qualitative and quantitative analysis.

Based on the above, in the biosensor provided by some embodiments described above, the first electrodes and the second electrodes are arranged alternately with each other, where the first electrodes are connected in parallel with each other, the second electrodes are connected in parallel with each other, and the extending direction of the channel is interlaced with the extending direction of the first electrodes and the second electrodes, so that the reaction efficiency and the electron transfer efficiency can be increased, thereby achieving the detection effects of high speed and high sensitivity.

Although the present disclosure has been disclosed with the above embodiments, it is not intended to limit the present disclosure. Any person of ordinary skill in the art can make some changes and modifications without departing from the spirit and scope of the present disclosure. Therefore, the protection scope of the present disclosure shall be defined by the appended claims.

What is claimed is:

1. A biosensor, comprising:
a substrate, having a sampling region, a collecting region, and a measuring region connected to the sampling region and configured between the collecting region and the sampling region, wherein the substrate has a first groove configured in the sampling region;
a first electrode comprising a plurality of first strip patterns disposed on the measuring region of the substrate, wherein the plurality of first strip patterns are arranged in a first direction and electrically connected with each other in parallel;
a second electrode comprising a plurality of second strip patterns disposed on the measuring region of the substrate, wherein the plurality of second strip patterns are arranged in the first direction and electrically connected with each other in parallel, wherein the plurality of first strip patterns and the plurality of second strip patterns are arranged alternately with each other in the first direction;
a third electrode disposed on the sampling region of the substrate near a boundary of the measuring region, wherein the third electrode is configured in the first groove to monitor a flow condition of a liquid entering the biosensor from the first groove in the sampling region;
a material layer, disposed on the measuring region of the substrate and covering the plurality of first strip patterns and the plurality of second strip patterns, wherein the material layer comprises a channel exposed a portion of each of the plurality of first strip patterns and a portion of each of the plurality of second strip patterns, one end of the channel is connected to the sampling region and another end of the channel is connected to the collecting region, and an extending direction of the channel is interlaced with extending directions of the plurality of first strip patterns and the plurality of second strip patterns; and
a capture antibody, disposed on the plurality of first strip patterns exposed by the channel and the plurality of second strip patterns exposed by the channel.

2. The biosensor according to claim 1, further comprising:
a cover, disposed on the material layer and covering the measuring region; and
a first hydrophilic layer, disposed on a surface of the cover facing the channel.

3. The biosensor according to claim 1, wherein the collecting region comprises a second groove disposed in the substrate.

4. The biosensor according to claim 3, further comprising:
an absorbing material, disposed on a bottom surface and sidewalls of the groove.

5. The biosensor according to claim 4, further comprising:
a second hydrophilic layer, disposed on the absorbing material.

6. The biosensor according to claim 1, wherein the channel is S-shaped in the measuring region adjacent to the collecting region.

7. The biosensor according to claim 1, wherein a sum of lengths of portions of the channel that overlap with the plurality of first strip patterns and the plurality of second strip patterns in the extending direction of the channel is greater than or equal to 0.8 cm.

8. The biosensor according to claim 1, wherein a width of the channel is between 1.5 mm to 3 mm.

9. A biological detection method, comprising:
providing a biosensor according to claim 1;
providing a sample having an antigen to the sampling region and filling the channel with the sample such that the antigen binds to the capture antibody;
providing a voltage difference between the first electrode and the second electrode to cause an electrochemical reaction between the antigen and the capture antibody; and
collecting a current generated by the electrochemical reaction to obtain a concentration of the antigen corresponding to the current.

10. A biological detection method, comprising:
providing a biosensor according to claim 1;
providing a sample having an antigen to the sampling region and filling the channel with the sample such that the antigen binds to the capture antibody;
providing a detection antibody with an enzyme to the sampling region and filling the channel with the detection antibody such that the antigen binds to the detection antibody;
providing a cleaning solution into the channel;
providing an enzyme substrate into the channel to allow the enzyme substrate reacting with the enzyme to generate an enzyme product;
providing a voltage difference between the first electrode and the second electrode to cause an electrochemical reaction of the enzyme product; and
collecting a current generated by the electrochemical reaction to obtain a concentration of the antigen corresponding to the current.

* * * * *